United States Patent [19]

Holtkamp, Sr.

[11] Patent Number: Plant 7,007

[45] Date of Patent: Aug. 29, 1989

[54] AFRICAN VIOLET PLANT NAMED TAURUS

[76] Inventor: Reinhold Holtkamp, Sr., Werther Strasse 112, D4294 Isselburg, Fed. Rep. of Germany

[21] Appl. No.: 251,321

[22] Filed: Sep. 30, 1988

[51] Int. Cl.[4] ..... A01H 5/00
[52] U.S. Cl. ..... Plt./69
[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of african violet named Taurus characterized by its single, dark lilac flowers with darker center radiating into the 2 small petals; strong, upright flower stems that curve toward the center to form a compact bouquet above the leaves; bright green, slightly serrated girl-type leaves; profuse flowering, vigorous growth habit, flowering as early as 8–9 weeks after potting, and its long lasting and non-dropping flowers.

1 Drawing Sheet

The present invention comprises a new and distinct cultivar of african violet plant, botanically known as *Saintpaulia ionantha,* and hereinafter referred to by the cultivar name Taurus.

The new cultivar was referred to during the breeding and selection process by the designation I II/33 and is a product of a planned breeding program. The new cultivar was originated from a cross made by me in the controlled breeding program in Haffen, Federal Republic of Germany. The female, or seed parent was a cultivar designated F 38/6. The male, or pollen parent was a cultivar designated G 24/1.

Taurus was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Taurus has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Taurus, which in combination distinguish this african violet as a new and distinct cultivar:

(1) Strong, upright flower stems curving toward the center.
(2) Single dark lilac flowers with darker center.
(3) Profuse flowering.
(4) Each plant carries 8–9 and more upright flower stems each of which carries 6–8 and more flowers.
(5) Long lasting, non-dropping flowers.
(6) Vigorous grower.
(7) Very early bloomer with plant being saleable within 8–9 weeks after potting.
(8) Seed capsules push slightly through.

(9) Bright green girl-type leaf, wavy, slightly serrated with a greenish white center.
(10) After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural sunlight conditions at approximately 2 p.m. in Nashville, Tenn.

Botanical classification: *Saintpaulia ionantha,* Ramat., c.v. Taurus.

Parentage:

*Male parent.*—G 24/1.

*Female parent.*—F 38/6.

Propagation: The new cultivar holds its distinguishing characteristics through successive propagations by leaf cuttings.

Plant: From 8 to 10 cm tall when grown in pots, and approximately 18–20 cm in diameter when fully grown.

*Leaves.*—General form: Round to heart-shaped, girl-type. Diameter: 60–70 mm. Texture: Slightly velvety. Aspect: Slightly serrated, slightly hairy, bright greenish white center. Veins: Upperside: well visible, greenish white radiating from the center; underside: well pronounced, light green, shiny. Color (upperside): Yellow-Green Group 147 between A and B. Color (underside): Greyed-Green Group 194 D. Petiole: Strong upright, light green with purplish touch on side towards flowers, hairy.

*Flowers:* Buds: Bell-shaped, 8–9 mm just before opening, purple. Sepals: Five (5). Color: Purplish green. Calyx: Shape: Funnel-shaped. Aspect: Spear-shaped, hairy. Peduncle: Character: Strong upright, hairy. Color: Purplish brown. Individual flowers: Size 35–40 mm. Shape: Single violet-shaped (3 large and 3 small petals). Color (upperside): Purple-Violet Group 78 between B and C, center A. Under cooler temperatures and more intensive lighting, the dark lilac color tends to intensity. Color (underside): Purple-Violet Group 78 varying from B to D. Borne: Each flower stem carries 6–8 and more flowers on strong, upright peduncles that are free standing above the leaves, thereby forming a compact bouquet. Flowering Habit: Flowers 10–11 weeks after potting.

*Reproductive organs.*—Stamens: Two (2). Anthers: 2 composed of 4 anther cells, seed capsule pushes slightly through. Filaments: Yellowish green, 4–5 mm long. Pollen color: Yellow Group 7 A. Styles: 7 mm long, purple, base of ovary light green and hairy.

*Roots.*—Normally developed, white when young, turning slightly brownish when older.

Disease resistance: Good.

General observations: Taurus has a very attractive appearance due to its bright green, slightly serrated leaves with a light green center. Taurus is a very early bloomer: A tight bouquet of flowers free standing above the leaves develops already after approximately 8–9 weeks. Each of the 8–9 and more strong flower stems carries 6–8 and more dark lilac, single violet-shaped flowers. In the center of the flower the dark lilac color is even darker and radiates into the two small petals. Occasionally, 1–2 additional very small petals may develop. The flowers are long-lasting and non-dropping.

I claim:

1. A new and distinct cultivar of african violet named Taurus, as described and illustrated, and particularly characterized by its single, dark lilac flowers with darker center radiating into the 2 small petals; strong, upright flower stems that curve toward the center to form a compact bouquet above the leaves; bright green, slightly serrated girl-type leaves; profuse flowering, vigorous growth habit, flowering as early as 8–9 weeks after potting, and its long lasting and non-dropping flowers.

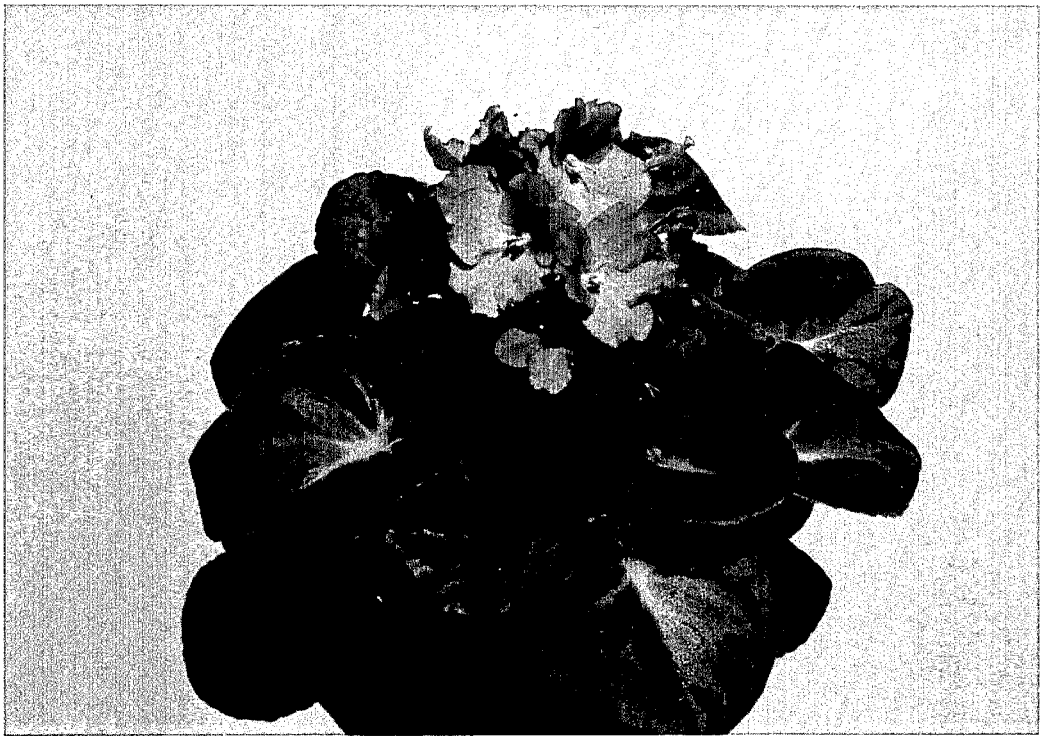

* * * * *